United States Patent
Lee et al.

(10) Patent No.: US 12,383,595 B2
(45) Date of Patent: Aug. 12, 2025

(54) COMPOSITION FOR PROMOTING AND IMPROVING SLEEP AND BEVERAGE CONTAINING SAME, AND MANUFACTURING METHOD THEREOF

(71) Applicant: ROMANSIVE CO., LTD., Seoul (KR)

(72) Inventors: Soo Hyun Lee, Seoul (KR); Ju Hui Choi, Chungju-si (KR)

(73) Assignee: ROMANSIVE CO., LTD., Seoul (KR)

( * ) Notice: Subject to any disclaimer, the term of this patent is extended or adjusted under 35 U.S.C. 154(b) by 0 days.

(21) Appl. No.: 17/923,721

(22) PCT Filed: Jul. 7, 2022

(86) PCT No.: PCT/KR2022/009833
§ 371 (c)(1),
(2) Date: Nov. 7, 2022

(87) PCT Pub. No.: WO2023/282655
PCT Pub. Date: Jan. 12, 2023

(65) Prior Publication Data
US 2024/0269218 A1    Aug. 15, 2024

(30) Foreign Application Priority Data

Jul. 7, 2021 (KR) ......................... 10-2021-0088845
Jan. 19, 2022 (KR) ......................... 10-2022-0007548
Jul. 6, 2022 (KR) ......................... 10-2022-0083340

(51) Int. Cl.
| | | |
|---|---|---|
| *A61K 36/725* | (2006.01) | |
| *A61K 9/00* | (2006.01) | |
| *A61K 31/197* | (2006.01) | |
| *A61K 33/06* | (2006.01) | |
| *A61K 36/185* | (2006.01) | |
| *A61P 25/20* | (2006.01) | |

(52) U.S. Cl.
CPC .......... *A61K 36/725* (2013.01); *A61K 9/0056* (2013.01); *A61K 31/197* (2013.01); *A61K 33/06* (2013.01); *A61K 36/3486* (2024.05); *A61P 25/20* (2018.01); *A61K 2236/19* (2013.01)

(58) Field of Classification Search
None
See application file for complete search history.

(56) References Cited

FOREIGN PATENT DOCUMENTS

| | | |
|---|---|---|
| CN | 109645280 A | 4/2019 |
| KR | 10-2016-0077727 A | 7/2016 |
| KR | 10-2018-0108515 A | 10/2018 |
| KR | 10-2019-0133552 A | 12/2019 |

OTHER PUBLICATIONS

International Preliminary Report on Patentability dated Dec. 14, 2023 with a Translation of the Written Opinion of the International Searching Authority in Application No. PCT/KR2022/009833.
International Search Report dated Oct. 13, 2022 in Application No. PCT/KR2022/009833.
"Overcoming Insomnia: Nutrients and Plant-Based Bioactive Phytochemicals that Help Relieve Insomnia", Naver Blog, Nov. 6, 2017, pp. 1-46 (46 pages).

*Primary Examiner* — Michael V Meller
(74) *Attorney, Agent, or Firm* — Sughrue Mion, PLLC

(57) ABSTRACT

The present invention relates to a composition for promoting and improving sleep comprising lactic acid bacteria fermented extract for sanjoin extract as an active ingredient. Sanjoin extract according to the present invention showed an increase in the content of spinosin and an increase in the content of glycine related to sleep promotion and improvement effects through lactic acid bacteria fermentation. In addition, by confirming the excellent sleep promotion and improvement effect by the mixed fermented beverage prepared by further mixing hop extract, L-theanine and magnesium, etc. with the lactic acid bacteria fermented sanjoin extract of the present invention, sleep promotion and It can be usefully used in various health processed foods that can help improve.

7 Claims, 4 Drawing Sheets

[FIG. 1]
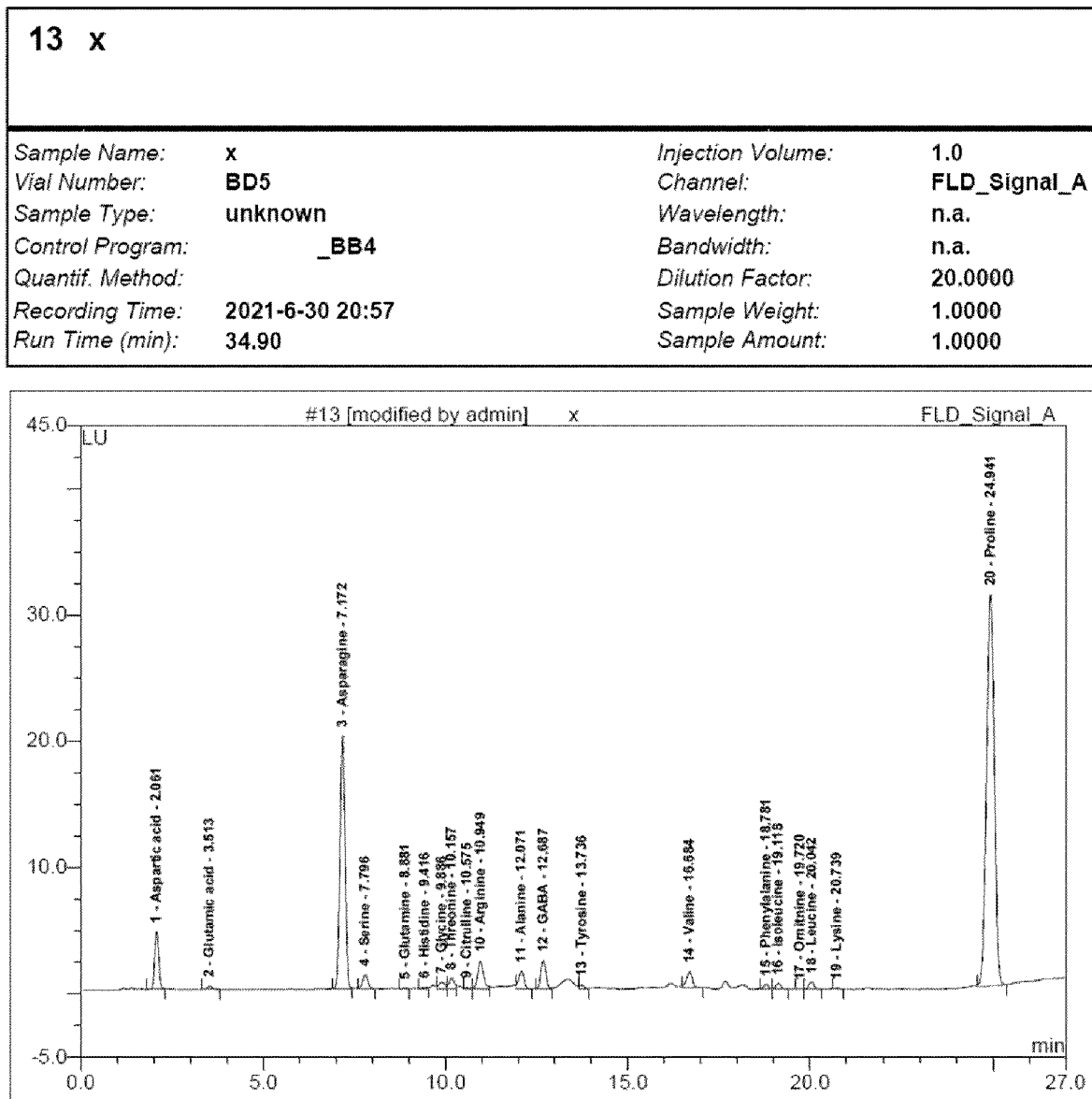

[FIG. 2]
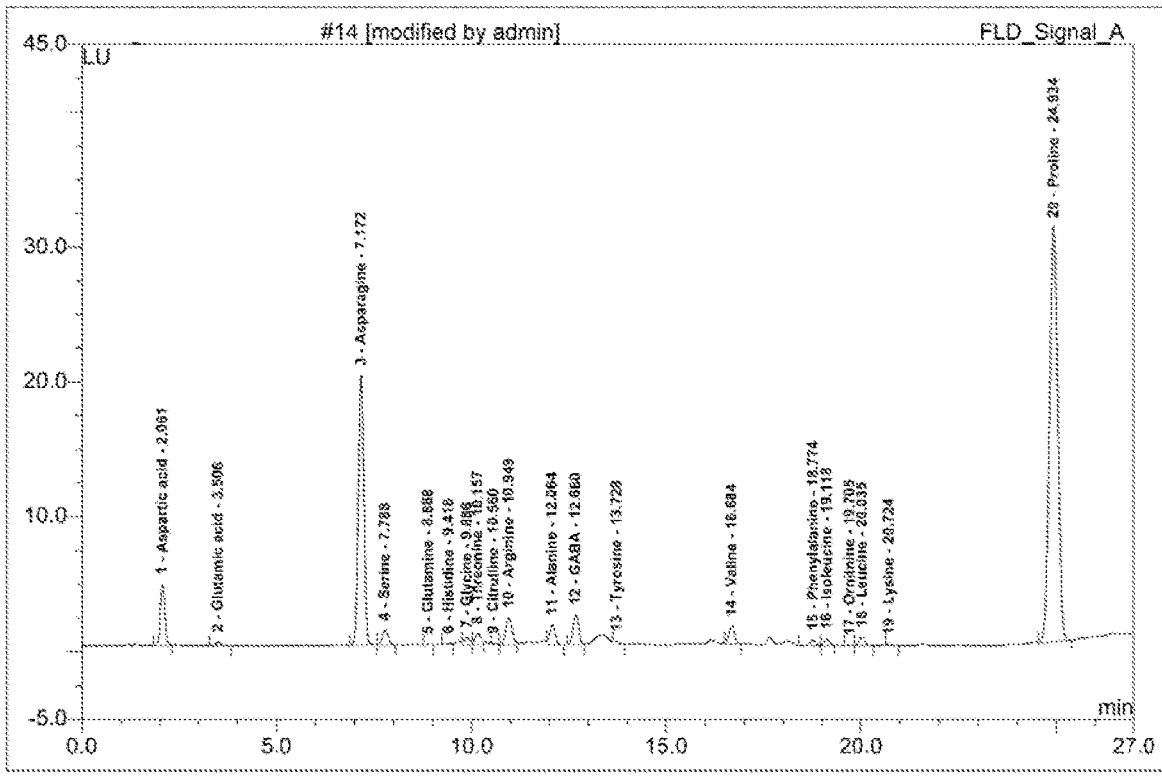

【FIG. 3】
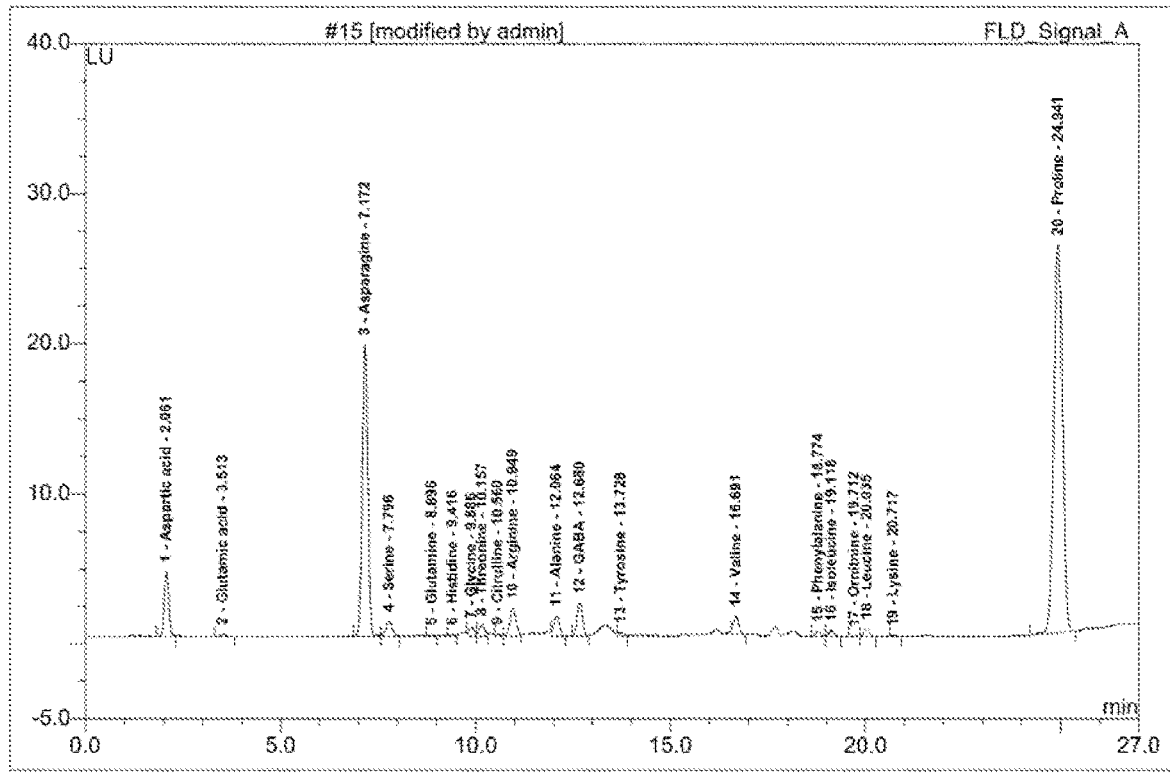

【FIG. 4】
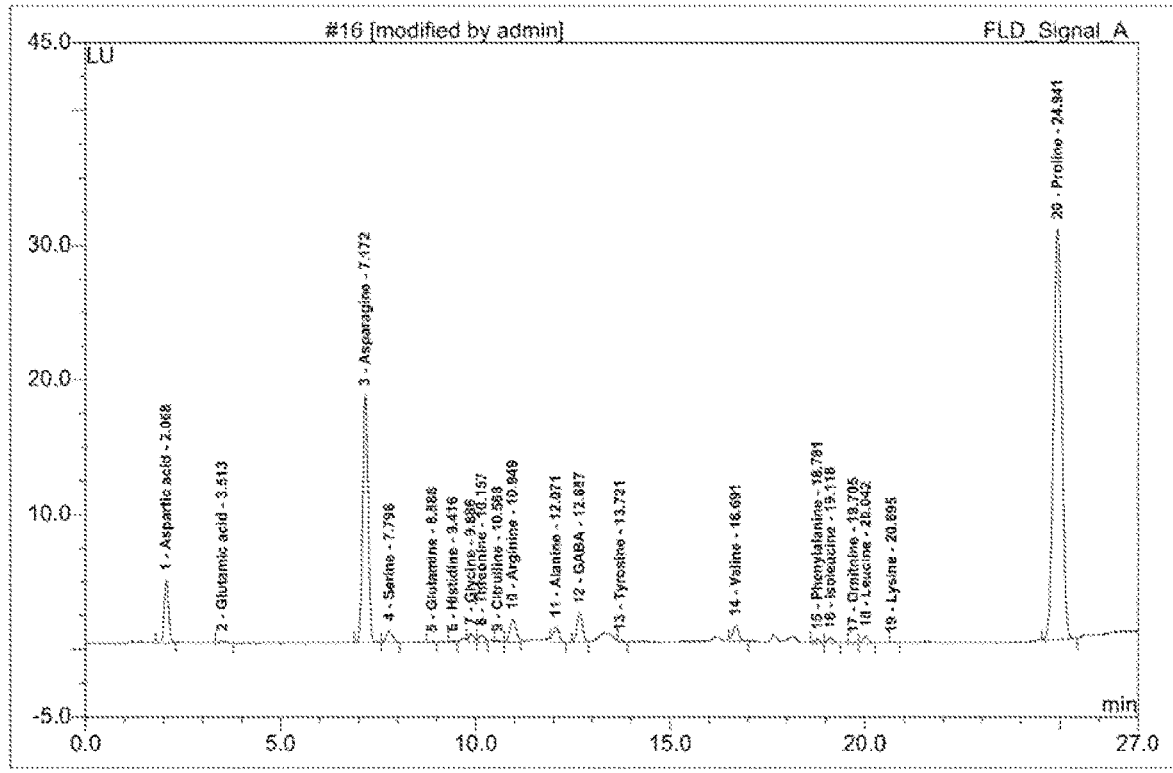

COMPOSITION FOR PROMOTING AND IMPROVING SLEEP AND BEVERAGE CONTAINING SAME, AND MANUFACTURING METHOD THEREOF

CROSS REFERENCE TO RELATED APPLICATIONS

This application is a National Stage of International Application No. PCT/KR2022/009833, filed Jul. 7, 2022, claiming priority to Korean Patent Application No. 10-2021-0088845, filed Jul. 7, 2021, Korean Patent Application No. 10-2022-0007548, filed Jan. 19, 2022 and Korean Patent Application No. 10-2022-0083340, filed Jul. 6, 2022, the entire disclosures of which are incorporated herein by reference.

TECHNICAL FIELD

The present disclosure relates to a composition for promoting and improving sleep, more particularly to a beverage containing a composition for promoting and improving sleep and a method for preparing the same.

BACKGROUND ART

According to the data of the National Health Insurance Service, the number of patients with sleep disorder in Korea has increased by 8% per year from 2014 to 2018 and by 13% in 2019, with 640,000 patients treated for sleep disorder. In 2020, the patients with sleep disorder have increased rapidly associated with the COVID-19 pandemic due to mental factors such as stress, anxiety, etc., change in lifestyles and decreased activities.

As sleeping drugs, benzodiazepine-based drugs, non-benzodiazepine-based drugs or antidepressants such as benzodiazepine receptor agonists are commonly prescribed. However, these drugs have the risk of tolerance and dependence when used for a long time, which result in difficulties in everyday lives. Additionally, they often cause other problems such as cognitive disorder, depression, etc.

Accordingly, although many people suffer from sleep disorder, a suitable solution is not provided due to the concern of side effects, tolerance, dependence, etc. Because about 40% of acute insomnia turns into chronic insomnia, it is important to diagnose and treat sleep disorder early, and the development of a natural sleeping solution with no risk of side effects, tolerance and dependence is urgent.

DISCLOSURE

Technical Problem

The inventors of the present disclosure have researched whether a lactic acid bacteria-fermented zizyphus seed extract can be used to promote and improve sleep, and have identified that the lactic acid bacteria-fermented zizyphus seed extract of the present disclosure has increased contents of spinosin and glycine, which are associated with the effect of promoting and improving sleep. In addition, they have verified and identified through experiments that a fermented beverage prepared by mixing the lactic acid bacteria-fermented zizyphus seed extract of the present disclosure with a hop extract, L-theanine, magnesium, etc. has superior effect of promoting and improving sleep, and have completed the present disclosure.

The present disclosure is directed to providing a composition for promoting and improving sleep, which contains a lactic acid bacteria fermentation product of a zizyphus seed extract as an active ingredient, and a beverage containing the same.

The present disclosure is also directed to providing a method for preparing a composition for promoting and improving sleep.

The present disclosure is also directed to providing a food for promoting and improving sleep, which contains the composition for promoting and improving sleep. Other purposes and technical features of the present disclosure will be presented more specifically by the following detailed description, claims and drawings.

Technical Solution

In an aspect, the present disclosure provides a composition for promoting and improving sleep, which contains a lactic acid bacteria fermentation product of a zizyphus seed extract as an active ingredient.

In an exemplary embodiment of the present disclosure, the lactic acid bacteria may include one or more lactic acid bacteria selected from a group consisting of *Lactobacillus plantarum, Lactobacillus brevis, Lactobacillus paracasei, Lactobacillus casei* and *Lactobacillus lactis*.

In an exemplary embodiment of the present disclosure, the composition may have increased contents of spinosin and glycine as compared to before the lactic acid bacteria fermentation.

In an exemplary embodiment of the present disclosure, the content of spinosin may be increased by 5% or more as compared to before the lactic acid bacteria fermentation, or the content of glycine content may be increased by 10% or more as compared to before the lactic acid bacteria fermentation.

The content of spinosin may be increased specifically by 7% or more, more specifically by 10% or more. The content of glycine content may be increased specifically by 13% or more, more specifically by 15% or more.

In an exemplary embodiment of the present disclosure, the extract may be extracted using water including purified water, an organic solvent or a mixture thereof as an extraction solvent.

In the present disclosure, the organic solvent may be selected from a group consisting of a $C_1$-$C_4$ alcohol, n-hexane, ether, glycerol, propylene glycol, butylene glycol, ethyl acetate and methyl acetate, although not being limited thereto. The $C_1$-$C_4$ alcohol may be specifically ethanol or methanol, although not being limited thereto.

In another aspect, the present disclosure provides a method for preparing a composition for promoting and improving sleep, which includes:
(a) a step of obtaining a liquid zizyphus seed extract by extracting roasted zizyphus seed with an extraction solvent;
(b) a step of sterilizing the liquid zizyphus seed extract obtained in the step (a); and
(c) a step of fermenting the liquid zizyphus seed extract sterilized in the step (b) by inoculating lactic acid bacteria.

In an exemplary embodiment of the present disclosure, the step (a) may further include, after extracting the roasted zizyphus seed with an extraction solvent, a step of preparing a powder by filtering and spray-drying the extract and then diluting with purified water.

In another aspect, the present disclosure provides a beverage for promoting and improving sleep, which contains the composition for promoting and improving sleep.

Advantageous Effects

A superior effect of promoting and improving sleep is expected for a food or a beverage prepared using a composition for promoting and improving sleep proposed in the present disclosure.

In addition, because the composition for promoting and improving sleep proposed in the present disclosure uses a natural extract without containing special chemical ingredients, it can be taken safely with no risk of side effects, tolerance and dependence.

In addition, the composition for promoting and improving sleep and a method for preparing the same proposed in the present disclosure can provide much better effect as compared to the preceding attempts to promote sleep using similar ingredients.

BRIEF DESCRIPTION OF DRAWINGS

FIG. 1 shows an HPLC analysis result for a zizyphus seed extract before lactic acid bacteria fermentation according to the present disclosure depending on amino acid contents.

FIG. 2 shows an HPLC analysis result for a zizyphus seed extract which has been lactic acid bacteria-fermented for 12 hours according to the present disclosure depending on amino acid contents.

FIG. 3 shows an HPLC analysis result for a zizyphus seed extract which has been lactic acid bacteria-fermented for 24 hours according to the present disclosure depending on amino acid contents.

FIG. 4 shows an HPLC analysis result for a zizyphus seed extract which has been lactic acid bacteria-fermented for 48 hours according to the present disclosure depending on amino acid contents.

BEST MODE

The specific exemplary embodiments described in the present specification are merely exemplary embodiments or examples of the present disclosure and the scope of the present disclosure is not limited by them. It will be obvious to those skilled in the art that the changes and other uses of the present disclosure do not depart from the scope of the present specification described in the appended claims.

Hereinafter, the specific exemplary embodiments of the present disclosure will be described together with zizyphus seed and its extract, which are one of the main ingredients.

Zizyphus seed is the seed of jujube (*Zizyphus jujuba* Miller var. *spinosa* Hu ex H. F. Chou) of the family Rhamnaceae. It has a flat round or oval shape, with a length of 5-9 mm, a width of 5-7 mm and a thickness of 3 mm. It has a peachblow or purplish brown color. One side is even and the other side is uneven. It has a vertically protruding stripe pattern at the center. There is a concave and linear point on one end, and a protruding small point on the other.

The pharmacological activities of the zizyphus seed include anti-inflammatory, liver-protecting, memory-improving, anti-anxiety, antioxidant (in gastritis and gastric ulcer) and anticancer activities. Also, it has a pharmacological efficacy for the central nervous system, significantly reduces endurance time in the rotarod test and significantly decreases onset time in a sodium thiopental-induced sleep test.

The ingredients of the zizyphus seed include jujuboside A, jujuboside A2, jujuboside B, betulin, betulinic acid, spinosin, isospinosin, nicotiflorin, 6'''-p-coumaroylspinosin, hovetrichoside C, daucosterol, butyl β-D-fructofuranoside, magnoflorine, zizyphus saponin III, ursolic acid, pomolic acid, adenosine, alphitolic acid, etc.

Based on the previous studies on efficacy and ingredients, the active markers of the zizyphus seed may be commonly regarded as spinosin, betulinic acid and jujuboside A. When considering only the action on the central nervous system, flavonoid C-glycoside, which is a spinosin, may be regarded as the only marker compound (source: Institute of Herbal Medicine, National Institute of Food and Drug Safety, Ministry of Food and Drug Safety).

The zizyphus seed has been mainly used as a medicinal herb and contains fatty oil (about 31.8%).

However, because some people feel unpleasant with the weak oily smell and characteristic sour taste of zizyphus seed, it has been necessary to process it into a beverage preferred by consumers while maintaining or enhancing its functional ingredients.

Conventionally, medicinal herbs with sweet taste, such as longan or licorice, have been added to solve this problem. However, the characteristic taste of the medicinal herbs has limited the commercialization of the beverage.

Fermentation refers to a metabolic process that produces chemical changes in organic substances through the action of enzymes. Through the fermentation process, various characteristics and new products which were nonexistent in the raw material are obtained. The fermented food provides the functions of increased digestibility, increased content of water-soluble proteins, increased bioavailability, increased antioxidant activity, synthesis of nutrients, improved immune function, etc. Special physiological functions can be expected from low-molecular-weight substances that can be obtained through fermentation.

The inventors of the present disclosure have identified that the effect of promoting and improving sleep is enhanced when a substance extracted from zizyphus seed is fermented using lactic acid bacteria and have completed the present disclosure. Specifically, it has been identified that the lactic acid bacteria-fermented zizyphus seed extract presented in the present disclosure has increased contents of spinosin and glycine, which are associated with the effect of promoting and improving sleep.

The inventors of the present disclosure have also identified that a better effect of promoting and improving sleep can be achieved by preparing a fermented beverage by mixing the lactic acid bacteria-fermented zizyphus seed extract with a hop extract, L-theanine, magnesium, etc.

It has been identified that the lactic acid bacteria fermentation product of a zizyphus seed extract according to the present disclosure has (i) an increased content of spinosin and (ii) an increased content of glycine, which are associated with the effect of promoting and improving sleep.

(i) Spinosin is known as the representative active marker of the zizyphus seed that acts on the central nervous system. In an exemplary embodiment of the present disclosure, the lactic acid bacteria fermentation of a zizyphus seed extract increases the content of spinosin and, through this, a superior effect of promoting and improving sleep can be expected.

Spinosin (6-(2-O-beta-D-glocopyranosyl-beta-D-glucopyranosyl)-5-hydroxy-2-(4-hydroxyphenyl)-7-methoxy-4H-1-benzopyran-4-one) is a compound represented by Chemical Formula 1.

[Chemical Formula 1]

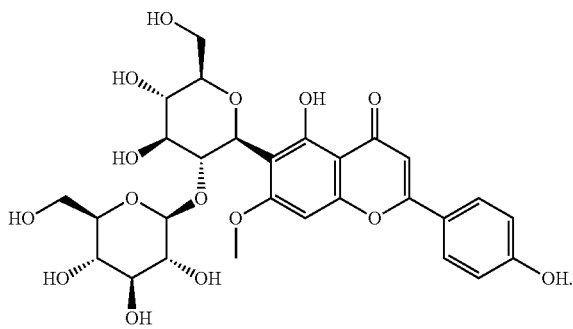

The spinosin represented by Chemical Formula 1 can be obtained from various medicinal herbs. For example, the spinosin may be obtained from *Zizyphus jujuba* Mill var. *inermis*, *Zizyphus jujuba* Mill var. *hoonensis*, *Zizyphus jujuba* Mill var. *spinosa*, *Passiflora edulis flavicarpa*, *Cayaponia tayuya*, *Desmodium tortuosum*, *Wilbrandia ebracteata*, *Strophioblachia fimbricalyx*, *Clutia abyssinica*, *Saccharopolyspora spinosa* or a mixture thereof. Specifically, it may be from obtained from zizyphus seed, which is the seed of *Zizyphus jujuba* Mill var. *spinosa*, as in the present disclosure.

In another exemplary embodiment of the present disclosure, the lactic acid bacteria fermentation may be performed on an extract of a medicinal herb containing spinosin in addition to the zizyphus seed extract.

In another exemplary embodiment of the present disclosure, the lactic acid bacteria fermentation may be performed after adding commercially available spinosin to the zizyphus seed extract to satisfy the required content. As described above, the spinosin is a natural ingredient contained in medicinal herbs and can provide the desired effect of improving sleep with no side effect on the human body.

(ii) Glycine is known as the only amino acid having no chiral carbon atom. Glycine is also called glycocol or aminoacetic acid and can be extracted from the hydrosylates of proteins.

The quantity of glycine synthesized in the body is limited to about 2.5 g per day, and the insufficient amount should be compensated for from food. Glycine is effective in improving sleep and recovering from obsession, schizophrenia, stroke, etc. Specifically, it may mediate the prevention of muscle movement during REM (rapid eye movement) sleep.

It has been identified that the lactic acid bacteria fermentation product of a zizyphus seed extract presented in the present disclosure has an increased content of glycine. Therefore, an effect of promoting and improving sleep can be expected in combination with the increased content of spinosin described above. In addition, with increased antioxidant activity and an increased content of polyphenols, the applicability as various health supplement foods can also be expected.

In an exemplary embodiment of the present disclosure, the extract may be extracted using water, ethanol or a mixture thereof as an extraction solvent. In the present disclosure, the "extract" refers to a substance extracted or isolated from a raw material by any method, and includes an extract extracted from the raw material, a concentrate that can be obtained therefrom and a dried product and powder of the concentrate, without limitation. The extract may be obtained by any known extraction method such as hot water extraction, solvent extraction, cold extraction, reflux extraction, ultrasonic extraction, etc., although not being limited thereto.

In the present disclosure, the zizyphus seed extract may be prepared into a powder form through an additional process such as vacuum concentration, freeze-drying, spray-drying, etc. In addition, the zizyphus seed extract of the present disclosure may be prepared by a common method known in the art, i.e., by using a common solvent under common temperature and pressure conditions.

In the present disclosure the "fermentation product" may be a fermentation product obtained by culturing lactic acid bacteria in a zizyphus seed extract, a concentrate of the fermentation product, a filtrate of the fermentation product, a concentrated filtrate of the fermentation product, or a drying product of the filtrate of the fermentation product. It may contain the lactic acid bacteria or may be a filtrate with the lactic acid bacteria removed after the fermentation. In addition, the fermentation product may be, for example, a liquid or a solid without limitation in form.

In an exemplary embodiment of the present disclosure, the composition using the zizyphus seed extract may contain one or more of a hop (*Humulus lupulus*) extract, L-theanine and magnesium.

In addition, a fermented beverage prepared by mixing the lactic acid bacteria-fermented zizyphus seed extract of the present disclosure with a hop extract, L-theanine, magnesium, etc. can be usefully used in various processed health foods that can be helpful in promoting and improving sleep because it has been identified to exhibit superior effect of promoting and improving sleep.

Hop (*Humulus lupulus*) is a plant in the genus *Humulus* of the family Cannabaceae with a height of 6-12 m, which is distributed in Europe and Asia. It is mainly used in beer and has been cultivated in Germany since the late 8th century. Its hypnotic was discovered from the fact that sleep is induced in hop harvesters, and the German Committee E approved the use of hop for treatment of neurosis and insomnia. Among the main active ingredients of hop, α-bitter acids (humulones) and β-acids (lupulones) are known to have sedative and antidepressant effects and xanthohumol is known to bind to the GABA receptors.

L-Theanine is contained mainly in foods such as green tea, black tea, mushroom, etc. and is approved as a safe functional ingredient by the Ministry of Food and Drug Safety and the FDA. It has been proven to reduce stress-induced tension in clinical trials. It is known to inhibit glutamate, which is an excitatory neurotransmitter, and increase the production of alpha waves in the brain.

Magnesium is called a natural sedative. As an anti-stress mineral, it relaxes the excited state of the mind. It is also a cofactor of more than 300 enzyme systems. It relaxes muscles and also is an essential nutrient for production of GABA.

The composition for promoting and improving sleep of the present disclosure, which further contains one or more of the hop (*Humulus lupulus*) extract, L-theanine and magnesium, may be prepared into various processed health foods having superior effect of promoting and improving sleep.

The food containing the composition of the present disclosure includes, for example, various foods, beverages, gums, teas, vitamin complexes, health supplements, etc., and may be prepared into a powder, a granule, a tablet, a capsule or a beverage.

The food of the present disclosure may further contain, in addition to the composition for promoting and improving sleep as an essential ingredient, a sitiologically acceptable food additive, e.g., a natural carbohydrate, a flavorant, etc.

The natural carbohydrate may be a common sugar such as a monosaccharide such as glucose, fructose, etc., a disaccharide such as maltose, sucrose, etc. and a polysaccharide such as cyclodextrin, etc. or a sugar alcohol such as xylitol, sorbitol, erythritol, etc.

The flavorant may be a natural flavorant such as thaumatin, rebaudioside A, glycyrrhizin, stevia extract, etc. or a synthetic flavorant such as saccharin, aspartame, etc.

In addition, the food presented in the present disclosure may contain various nutrients, vitamins, minerals, flavorants such including synthetic flavorants and natural flavorants, colorants, extenders, pectic acid and its salts, alginic acid and its salts, organic acids, protective colloidal thickeners, pH control agents, stabilizers, antiseptics, glycerin, alcohols, carbonating agents used in carbonated beverages, etc. In addition, the food of the present disclosure may also contain a pulp for preparing a natural fruit juice, a fruit juice beverage, a vegetable beverage, etc.

These ingredients may be used either independently or in combination.

EXAMPLES

Throughout the present specification, the '%' used to describe the concentration of a specific substance is (wt/wt) % for solid/solid, (wt/vol) % for solid/liquid, and (vol/vol) % for liquid/liquid, unless mentioned otherwise.

(1) Investigation of Increased Spinosin Content in Fermentation Product of Zizyphus Seed After grinding zizyphus seed into powder and adding water at a volume ratio of 1:4 (zizyphus seed:water), different lactic acid bacteria were inoculated. Then, after performing fermentation at a temperature slightly higher than room temperature for 72 hours, the liquid phase was separated using a gauze and then impurities were removed through centrifugation.

Then, after filtering the liquid phase once again with a 0.45-μm PVDF filter, the remaining solid phase was reconstituted in MeOH using Speed Vac, which was filtered once again with a 0.45-μm PVDF filter and then analyzed by LC-MS. The LC-MS analysis conditions are as follows.

Column: AcQuity UPLC BEH C18 column (1.7 μm, 100 mm×2.1 mm)
Flow rate: 0.3 mL/min
Ionization mode: NEG
Injection volume: 5 μL For each sample, the increase in spinosin content after the inoculation of lactic acid bacteria and fermentation was investigated for a total of 3 times and then averaged. The result is presented in Table 1. In Table 1, control denotes a control sample with no bacterial inoculation, brevis denotes a sample to which Lactobacillus brevis was inoculated, and lactics denotes another sample to which Lactobacillus lactis was inoculated. Experiments were conducted using various lactic acid bacteria, but only the results for the two lactic acid bacteria will be described.

TABLE 1

| Sample type | Calc (μg/ml) | Average (μg/ml) |
|---|---|---|
| Control 1 | 16.398 | 16.820 |
| Control 2 | 17.606 | |
| Control 3 | 16.456 | |
| Brevis 1 | 18.378 | 18.192 |

TABLE 1-continued

| Sample type | Calc (μg/ml) | Average (μg/ml) |
|---|---|---|
| Brevis 2 | 18.230 | |
| Brevis 3 | 17.966 | |
| Lactis 1 | 18.162 | 17.897 |
| Lactis 2 | 17.977 | |
| Lactis 3 | 17.553 | |

It was confirmed that brevis sample and the lactis sample have increased spinosin contents as compared to the control sample.

(2) Investigation Effects of Fermentation Product of Zizyphus Seed Extract

Step 1: Preparation of Zizyphus Seed Extract (Examples 1-3)

Roasted zizyphus seed was extracted at room temperature using a mixture solvent of water and ethanol. After filtering the extract and preparing into powder through spray-drying, a liquid zizyphus seed extract was obtained by diluting in purified water to a concentration of 25%.

Step 2: Sterilization of Zizyphus Seed or Zizyphus Seed Extract

The liquid zizyphus seed extract obtained in the step 1 was sterilized at a temperature of 100° C. or higher for several minutes.

Step 3: Culturing of Lactic Acid Bacteria

Each of Lactobacillus plantarum, Lactobacillus brevis, Lactobacillus paracasei, Lactobacillus casei and Lactobacillus lactis was inoculated to an MRS medium that had been sterilized for several minutes at a temperature of 100° C. or higher and then cultured for several hours at a temperature slightly higher than room temperature. The culture was centrifuged (4° C., 20000 rpm, 15 minutes) and then washed twice with a PBS buffer.

Step 4: Preparation of Lactic Acid Bacteria-Fermented Zizyphus Seed Extract

After preparing a lactic acid bacteria mixture solution by mixing the Lactobacillus plantarum, Lactobacillus brevis, Lactobacillus paracasei, Lactobacillus casei and Lactobacillus lactis washed in the step 3 in purified water, the lactic acid bacteria mixture solution was inoculated at 1% based on the zizyphus seed extract sterilized in the step 2. Then, a lactic acid bacteria-fermented zizyphus seed extract was prepared by conducting fermentation for 12 hours at a temperature slightly higher than room temperature. The lactic acid bacteria-fermented zizyphus seed extract sample was analyzed while varying the fermentation time.

[Test Example 1] Analysis of Contents of Amino Acids and Spinosin in Lactic Acid Bacteria-Fermented Zizyphus Seed Extract Depending on Fermentation Time The contents of amino acids including glycine and spinosin in the lactic acid bacteria-fermented zizyphus seed extract sample depending on fermentation time (0 hour, 12 hours, 24 hours and 48 hours) were quantitatively analyzed by HPLC, and the optimal conditions for extraction and content analysis were investigated. The analysis was conducted by the Chromatography Lab of the National Instrumentation Center for Environmental Management (NICEM) of Seoul National University.

Dionex Ultimate 3000 (Thremo Dionex, USA) was used for HPLC analysis of the contents of amino acids including glycine. The Inno C-18 column (Youngjinbiochrom, Koera' 4.6×250, 5 μm) was used. The column temperature was 40°

C. and the injection volume was 0.5 μL. A mixture of 40 mM sodium phosphate, acetonitrile and methanol was used as a mobile phase, and detection was made at 266-450 nm (FIGS. 1-4).

The result of analyzing the contents of amino acids under the HPLC analysis conditions described above is shown in Table 2.

TABLE 2

| Fermentation time (hr) content unit | 0 mg/L | 12 mg/L | 24 mg/L | 48 mg/L |
|---|---|---|---|---|
| Aspartic acid | 88.43 | 88.90 | 85.94 | 91.02 |
| Glutamic acid | 7.24 | 8.28 | 5.47 | 5.61 |
| Asparagine | 475.63 | 474.41 | 458.98 | 434.17 |
| Serine | 19.68 | 19.61 | 17.42 | 16.60 |
| Glutamine | 1.03 | 1.02 | 0.90 | 0.82 |
| Histidine | 4.99 | 4.82 | 4.00 | 3.92 |
| Glycine | 5.93 | 6.03 | 6.00 | 6.99 |
| Threonine | 15.80 | 15.62 | 13.50 | 10.67 |
| Citrulline | 1.54 | 2.14 | 2.47 | 2.80 |
| Arginine | 56.09 | 51.62 | 47.29 | 44.91 |
| Alanine | 18.69 | 19.62 | 17.69 | 15.69 |
| GABA | 32.78 | 32.71 | 32.39 | 31.88 |
| Tyrosine | 6.00 | 6.07 | 4.70 | 3.22 |
| Valine | 18.68 | 19.55 | 17.49 | 17.75 |
| Phenylalanine | 8.03 | 8.98 | 6.75 | 5.73 |
| Isoleucine | 6.95 | 7.30 | 6.41 | 5.89 |
| Ornitnine | 2.32 | 3.01 | 2.98 | 3.54 |
| Leucine | 9.39 | 10.25 | 8.29 | 7.94 |
| Lysine | 4.55 | 4.01 | 3.20 | 2.30 |
| Proline | 1335.49 | 1317.94 | 1061.08 | 1295.30 |

As can be seen from Table 2, the lactic acid bacteria-fermented zizyphus seed extract of the present disclosure showed an increased content of glycine, which is associated with the effect of promoting and improving sleep, as compared to the unfermented zizyphus seed extract.

The spinosin content was analyzed by HPLC using the Ultimate 3000 HPLC system (Thermo Dionex, USA). The Inno C-18 column (Youngjinbiochrom, Koera 4.6×250, 5 μm) was used. The column oven temperature was 45° C. and the injection volume was 10 μL. 0.1% trifluoroacetic acid and methanol were used as mobile phases, and detection was made at 335 nm.

The result of analyzing the spinosin content under the HPLC analysis conditions described above is shown in Table 3.

TABLE 3

| 발효시간(hr) | 0 | 12 | 24 | 48 |
|---|---|---|---|---|
| Spinosin 함량 (mg/L) | 19.06 | 19.29 | 20.17 | 20.05 |

As can be seen from Table 3, the zizyphus seed extract fermented with lactic acid bacteria for 12-48 hours showed an increased content of spinosin, which is associated with the effect of promoting and improving sleep, as compared to the unfermented zizyphus seed extract.

[Test Example 2] Investigation of Antioxidant Effect of Lactic Acid Bacteria-Fermented Zizyphus Seed Extract Depending on Fermentation Time In order to investigate the antioxidant effect of an unfermented zizyphus seed extract and the lactic acid bacteria-fermented zizyphus seed extract of the present disclosure, reactive oxygen species scavenging ratio was measured by DPPH assay.

After putting 100 μL of sample solutions of different concentrations in a test tube and adding 100 μL of ethanol and 50 μL of a 0.5 mM DPPH (1,1-diphenyl-2-picrylhydrazyl)/ethanol solution, absorbance was measured at 517 nm after keeping at room temperature (25° C.) for 30 minutes. Radical scavenging ratio (%) was calculated according to the following equation and the result is given in Table 4. The antioxidant ascorbic acid was used as a reference standard.

$$\text{Radical scavenging ratio (\%)} = (B - A)/B \times 100$$

A: absorbance of control well with no sample treatment
B: absorbance of test well with sample treatment

TABLE 4

| 발효시간(hr) | 0 | 12 | 24 | 48 |
|---|---|---|---|---|
| 평균 (mean) | 52.04819 | 51.16466 | 48.59438 | 53.25301 |
| 표준편차 (stdev) | 0.481928 | 1.452461 | 0.139121 | 0.417362 |

As can be seen from Table 4, the zizyphus seed extract fermented with lactic acid bacteria for 48 hours showed improved antioxidant activity as compared to the unfermented zizyphus seed extract.

[Test Example 3] Analysis of Total Polyphenol Content (TPC) of Lactic Acid Bacteria-Fermented Zizyphus Seed Extract Depending on Fermentation Time Total polyphenol content was measured according to the Folin-Denis method (Folin O. and Denis W., 1912, *J Biol Chem.* 12: 239-249). After adding 75 μL of methanol and 25 μL of a Folin-Ciocalteu phenol reagent to 25 μL of a sample diluted in methanol and conducting reaction for 6 minutes at room temperature, 100 μL of a saturated $Na_2Co_3$ solution was added. After mixing and keeping at room temperature for 90 minutes, absorbance was measured at 765 nm. A standard calibration curve was obtained using gallic acid as a standard, and the total polyphenol content of the extract was expressed as μg GAE (gallic acid equivalent)/mL. The standard calibration curve was obtained by measuring absorbance after treating with gallic acid of different concentrations (0.5, 1.0, 5.0, 10, 50 and 100 mg/mL). The total polyphenol content of the lactic acid bacteria-fermented zizyphus seed extract depending on fermentation time is given in Table 5.

TABLE 5

| 발효시간(hr) | 0 | 12 | 24 | 48 |
|---|---|---|---|---|
| 평균 (mean) | 2742.006 | 2654.874 | 2742.006 | 2829.138 |
| 표준편차 (stdev) | 65.349 | 78.53972 | 78.53972 | 75.45853 |

As can be seen from Table 5, the zizyphus seed extract fermented with lactic acid bacteria for 48 hours showed an increased total polyphenol content as compared to the unfermented zizyphus seed extract.

[Preparation Example] Preparation of Lactic Acid Bacteria-Fermented Beverage

A fermented beverage was prepared by adding a hop extract, L-theanine, magnesium, glycine and other additives for a beverage to a fermentation product of zizyphus seed or a zizyphus seed extract, which had been lactic acid bacteria-fermented.

[Test Example 4] Evaluation of Improvement of Sleep Disorder by Fermented Beverage of the Present Disclosure After recruiting 84 people suffering from sleep disorder, 10 people were selected randomly except for those who had the experience of taking psychoactive drugs or functional health foods in recent 6 months.

A control beverage was prepared by mixing 1 mg of a synthetic fruit flavor and 3 g of a sweetener in 110 mL of purified water. The fermented beverage containing the zizyphus seed extract fermented with lactic acid bacteria for 48 hours of Preparation Example was used as a test beverage.

The 10 people were divided into two groups of 5 people. Group 1 was asked to take 110 mL of the fermented beverage containing the lactic acid bacteria-fermented zizyphus seed extract prepared in Examples (test beverage) for a week 30 minutes before going to bed and then take the control beverage during the next week. Group 2 was asked to take the control beverage first for a week and then take the fermented beverage containing the lactic acid bacteria-fermented zizyphus seed extract (test beverage) during the next week. They were not informed of the test beverage. They were asked to record sleep logs every day and the sound sleep effect was evaluated on a weekly basis. The questionnaire was prepared based on the Korean version of the Pittsburgh Sleep Quality Index (PSQI-K), which is commonly used to evaluate sleep disorder. The result is shown in Tables 6-10.

TABLE 6

| weekly average | experimental group | control case |
| --- | --- | --- |
| within 15 minutes | 2 | 1 |
| 15 to 30 minutes | 5 | 2 |
| 30 minutes to 2 hours | 3 | 6 |
| more than 2 hours | 0 | 1 |

TABLE 7

|  | experimental group | control case |
| --- | --- | --- |
| 4 hours or less | 0 | 2 |
| 4 to 7 hours | 5 | 7 |
| more than 7 hours | 5 | 1 |

TABLE 8

|  | experimental group | control case |
| --- | --- | --- |
| Haven't been in the last week. | 3 | 2 |
| 1-2 times a week | 5 | 4 |
| 3 or more times a week | 2 | 4 |

TABLE 9

|  | experimental group | control case |
| --- | --- | --- |
| sleep satisfaction | 4.1 | 2.7 |

TABLE 10

|  | experimental group | control case |
| --- | --- | --- |
| Haven't been in the last week. | 4 | 2 |
| 1-2 times a week | 5 | 5 |
| 3 or more times a week | 1 | 3 |

As a result of evaluating the improvement of sleep disorder, it was confirmed that the fermented beverage containing the zizyphus seed extract fermented according to the present disclosure has superior effect of promoting and improving sleep as shown in Tables 6-10.

Although the specific exemplary embodiments of the present disclosure have been described in detail, it will be obvious to those having ordinary knowledge in the art that they are merely preferred exemplary embodiments and the scope of the present disclosure is not limited by them. Accordingly, it is to be understood that the substantial scope of the present disclosure is defined by the appended claims and their equivalents.

The invention claimed is:

1. A method for treating insomnia in a human in need thereof consisting essentially of administering to the human in need thereof a fermentation product of a ziziphus seed and a lactic acid bacteria selected from the group consisting of *Lactobacillus planatarum, Lactobacillis brevis, Lactobacillus paracasei, Lactobacillus casei* and *Lacotobacillis lactis*; maltose, cyclodextrin, and hops.

2. The method of claim 1, wherein the fermentation product has increased contents of spinosin and glycine as compared to before fermentation with the lactic acid bacteria.

3. The method of claim 2, wherein the content of spinosin is increased by 5% or more as compared to before fermentation with the lactic acid bacteria.

4. The method of claim 2, wherein the content of glycine content is increased by 10% or more as compared to before fermentation with the lactic acid bacteria.

5. The method of claim 1, wherein the fermentation product is prepared by extraction using water including purified water, an organic solvent or a mixture thereof as an extraction solvent.

6. The method of claim 5, wherein the organic solvent is one or more organic solvent selected from a group consisting of a C1-C4 alcohol, n-hexane, ether, glycerol, propylene glycol, butylene glycol, ethyl acetate and methyl acetate.

7. The method of claim 1, wherein the fermentation product further consists essentially of L-theanine and magnesium.

\* \* \* \* \*